United States Patent [19]

Mazurik et al.

[11] Patent Number: 5,037,394
[45] Date of Patent: Aug. 6, 1991

[54] DISPOSABLE INJECTION SYRINGE

[76] Inventors: Sergei M. Mazurik, ulitsa Lenina, 92, kv. 57; Andrei N. Sokolov, ulitsa 60 let SSSR, 3, kv. 20, both of Poltava, U.S.S.R.

[21] Appl. No.: 623,723
[22] PCT Filed: Oct. 16, 1989
[86] PCT No.: PCT/SU89/00266
    § 371 Date: Dec. 21, 1990
    § 102(e) Date: Dec. 21, 1990
[87] PCT Pub. No.: WO90/12613
    PCT Pub. Date: Nov. 1, 1990

[30] Foreign Application Priority Data

Apr. 24, 1989 [SU] U.S.S.R. ............................. 4682849

[51] Int. Cl.⁵ .............................................. A61M 5/00
[52] U.S. Cl. ...................................... 604/110; 604/218
[58] Field of Search ............... 604/110, 218, 220, 187, 604/208, 209, 210

[56] References Cited

U.S. PATENT DOCUMENTS 4,367,738  1/1983  Legendre et al. ............... 604/218
4,731,068  3/1988  Hesse ............................... 604/110
4,906,231  3/1990  Young ............................. 604/110

FOREIGN PATENT DOCUMENTS 8900432  1/1989  World Int. Prop. O. .......... 604/110

Primary Examiner—John D. Yasko
Attorney, Agent, or Firm—Fleit, Jacobson, Cohn, Price, Holman & Stern

[57] ABSTRACT

The invention relates to medical engineering.

A disposable injection syringe comprises a cylindrical body (1) accommodating a piston (2) with a rod (3). The rod (3) is of a shaped design and appears as a plurality cone frustums (7) arranged in series lengthwise the rod; a shaped hollow insert (8) is arranged concentrically to the rod, which insert is composed of two parts (8a,8b) and whose inner surface follows the outer surface of the rod (3), while its outer surface is formed by the surfaces of a plurality of cone frustums (9). A washer (10) is interposed between the piston (2) and the insert (8) concentrically to the rod (3), the side face of the washer being bevelled, while a collar (11) is provided on the inner surface of the body (1), one of the collar surfaces being bevelled so as to suit the bevelled surface of the washer (10).

The disposable injection syringe is applicable at any medical institutions and for individual use.

1 Claim, 3 Drawing Sheets

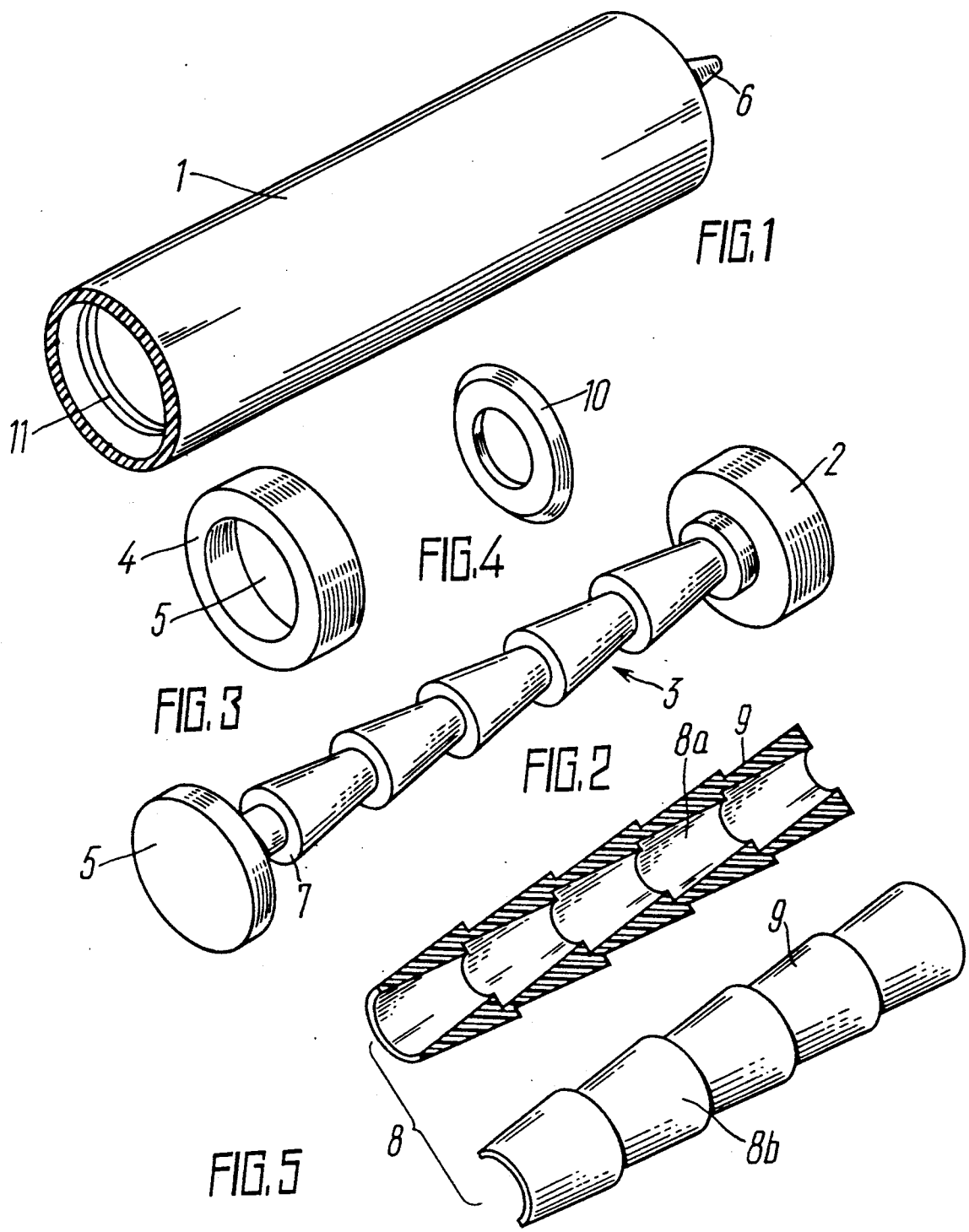

DISPOSABLE INJECTION SYRINGE

TECHNICAL FIELD

The invention relates generally to medical engineering and, more specifically, to disposable injection syringes.

World-wide diffusion of the epidemic of AIDS, injection syringes and needles being one of the principal ways of infection, poses a problem how to develop reliable constructions of disposable syringes, primary emphasis being placed on objective avoiding a possibility of reusing a disposable syringe.

PRIOR ART

Known in the art are disposable injection syringes, comprising a cylindrical body, a piston with a rod accommodated in said body, a hole in the rear face of the body for the piston rod to pass, and a needle fixing device in the front face of the body (cf., e.g., disposable syringes available from Trumo Europe Co., Belgium). The syringes discussed above differ practically in nothing from disposable syringes now in widespread use in medical practice, the sole exception being the fact that they are made of a cheaper material (that is, polymer) and are not therefore subject to sterilization. This means that the construction of the known disposable syringes enables them to be reused many times, which might occur on account of an inattentive or unscrupulous action of medical staff, or when injections are made by those who are in narcotic or alcoholic intoxication. All stated above proves to be of importance, since such cases are fraught with a danger of infection with the virus of AIDS, with that of infectious hepatitis, and of some other diseases.

One more prior art disposable syringe is known to comprise a cylindrical body accommodating a piston with a rod, a hole in the rear face of the body for the piston rod to pass, and a needle fixing device in the body front face (EP, A, 0282097).

In the syringe in question the needle is fixed in a washer located in the front portion of syringe body and capable of reciprocating along the syringe axis. The piston situated past the washer in the syringe body and rigidly coupled to the rod is not engaged with the washer but is provided with catches adapted for the piston to engage the washer when both of them interact with each other through their end faces. At the end of the injection when the piston and the washer get in contact with each other through their end faces, the piston becomes engaged rigidly, by means of the catches, with the washer, wherein the needly is fixed, with the result that any attempt to repeatedly draw a fresh portion of an injection substance in the syringe, the washer together with the needle is entrained by the piston into the syringe body. As soon as the needle gets inside cylindrical body of the syringe, it is offset with respect to the body axis so that any attempt to perform an injection will result in breakage of the injection needle.

However, such a construction leaves room for reusage of the syringe under consideration, since the piston is brought in engagement with the washer only when in its fully extended position in the front portion of the body. This causes the needle to be retracted into the body, whereby the syringe gets unfit for further use. Sould however the piston be not brought to the fully extended position during injection, the syringe can be applied for making an unlimited number of injections involving almost complete utilization of the syringe body holding capacity.

DISCLOSURE OF THE INVENTION

It is a primary and essential object of the invention to develop such a construction of a disposable injection syringe that would make impossible reusage of the syringe.

Said object is accomplished due to the fact that in a disposable injection syringe, comprising a cylindrical body accommodating a piston with a rod, a hole in the rear body face adapted for the rod to pass outside, and an injection needle fixing device located in the front body face, according to the invention, the rod is of a shaped design and is composed of a plurality of cone frustums arranged consecutively along the rod length and having their greater and lesser bases respectively equal to one another, said cone frustums facing the piston with their lesser bases, a shaped hollow insert is arranged in the syringe body concentrically to the piston rod so as to encompass the latter, said insert having joints located lengthwise the rod axis, which insert is composed of at least two parts, the inner surface of said insert follows the outer rod surface, while the outer insert surface is formed by the surfaces of a plurality of cone frustums arranged consecutively along the rod axis and coaxially therewith, the greater and the lesser bases of said cone frustums being respectively equal to one another, said cone frustums facing the piston with their greater bases, whereas the diameter of the hole in the rear face of the syringe body is selected to be approximately equal to a minimum outside diameter of the insert, a washer being interposed between the piston and the insert concentrically to the rod, the diameter of a hole in said washer being approximately equal to a minimum rod diameter, while the side face of said washer is bevelled so that the diameter of the washer face on the piston side exceeds the diameter of the washer face on the insert side, and a collar is provided on the body inner surface nearby the rear face thereof, said collar having one of its surfaces bevelled so as to suit the bevelled surface of said washer, while a minimum diameter of said collar is approximately equal to a minimum outside diameter of the washer.

A disposable injection syringe, according to the invention, makes impossible repeated injections, is simple in manufacture, and reliable in operation. Production cost of the disposable syringe, according to the invention, is not practically in excess of the production cost of the heretofore-known disposable injection syringes.

SUMMARY OF THE DRAWINGS

In what follows the invention is disclosed in a detailed description of a specific exemplary embodiment thereof given by way of illustration with reference to the accompanying drawings, wherein:

FIGS. 1, 2, 3, 4, 5 (a, b) represent an isometric view of a disassembled disposable injection syringe, according to the invention;

PREFERRED EMBODIMENT OF THE INVENTION

Figure 6:
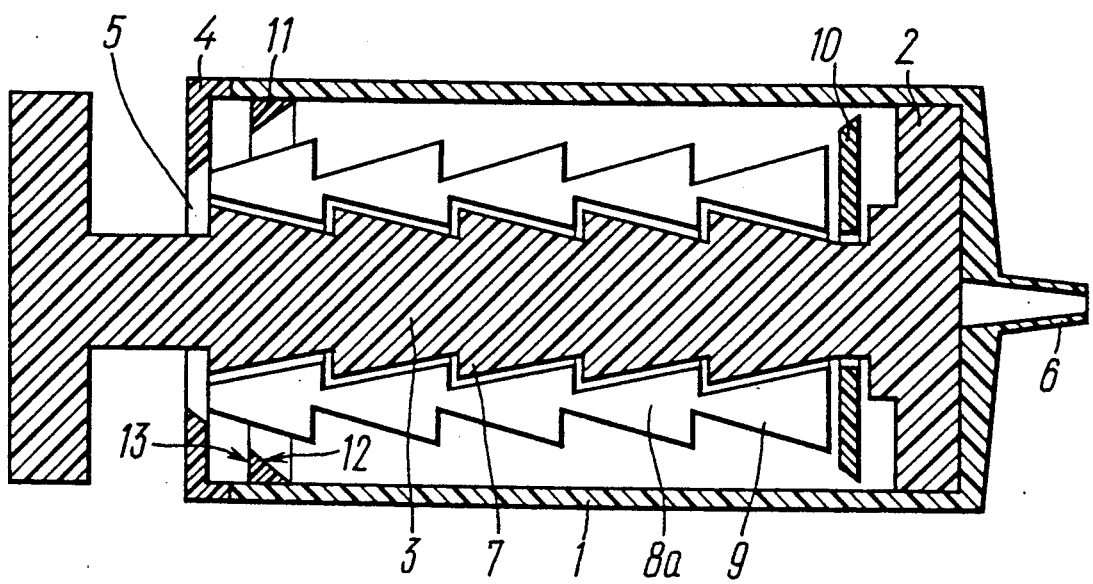
FIG. 6 is a longitudinal sectional view of a disposable injection syringe when in an initial position.

The disposable injection syringe, according to the invention, comprises a cylindrical body 1 (FIG. 1), which accommodates a piston 1 (FIGS. 2, 6) with a rod 3. The body 1 has a cover 4 (FIGS. 3, 6) located at the rear end thereof and fixed on the body i with the aid of a permanent joint. The cover 4 has a centre hole 5 for the rod 3 to pass. An injection needle fixing device, viz., a cannula 6 (FIGS. 1, 6) is provided at the front end of the body 1.

The rod 3 (FIGS. 2, 6) is of a shaped design and is composed of a plurality of cone frustums 7 arranged in series lengthwise the rod 3. The greater bases of the cone frustums are equal to one another, as well as the lesser bases thereof, with which the cone frustums face the piston 2. A shaped hollow insert 8 (FIGS. 5a, b, 6) is accommodated in the body 1 concentrically to the rod 3, said insert being split along the axis of the rod 3 and being composed of at least two parts 8a, 8b (which is the case with this particular exemplary embodiment of the invention. The insert 8 encomprasses the rod 3 and has its inner surface to the surface of the rod 3. The outer surface of the insert 8 is formed by the surfaces of cone frustums 9 arranged consecutively lengthwise the axis of the rod 3 coaxially thereto. The lesser bases of the cone frustums 9 are equal to ine another, as well as the greater bases thereof, with which the cone frustums face the piston 2. The diameter of the hole 5 in the cover 4 of the body 1 for the rod 3 to pass is selected to be approximately equal to a minimum outside diameter of the insert 8. A washer 10 (FIGS. 4, 6) is interposed between the piston 2 and the end of the insert 8 facing the piston 2 concentrically to the rod 3, an inside diameter of said washer being approximately equal to a minimum diameter of the rod 3. The outer side of the washer 10 is bevelled so that the diameter of the face of the washer 10 on the side of the piston 2 exceeds the diameter of the face of said washer on the side of the insert 8. A triangular collar 11 is provided on the inner surface of the syringe body 1 nearby the rear face thereof wherein the hole 5 is made. A surface 12 of said collar is bevelled at an angle lesser than 90° to the side surface of the body 1. A minimum diameter of the collar 11 is approximately equal to a minimum outside diameter of the washer 10. The bevelled surface 12 corresponds to the bevelled face of the washer 10 and is adapted to interact with said bevelled face. A surface 13 of the collar 11 is parallel to the end faces of the body 1. A distance between the surface 13 of the collar 11 and the inner surface of the cover 4 is equal to, or in excess of, the thickness of the washer 10.

The syringe is made of a polymer elastic material.

The disposable syringe, according to the invention, is applied as follows.

The order to draw an injection substance the rod 3 is extended from the syringe body 1 (FIG. 6). While, so doing, the cone frustums 9 of the insert 8, which is arranged concentrically to the rod 3, pass with a certain resistance through the hole 5 in the cover 4 of the syringe body 1 for the rod 3 to pass. This is attained due to a specific shape of the cone frustums 9 of the insert 8, whose minimum diameter is approximately equal to the diameter of the hole 5 in the cover 4 of the syringe body 1, as well as due to elasticity of the polymer material the syringe is made of.

Figure 7:
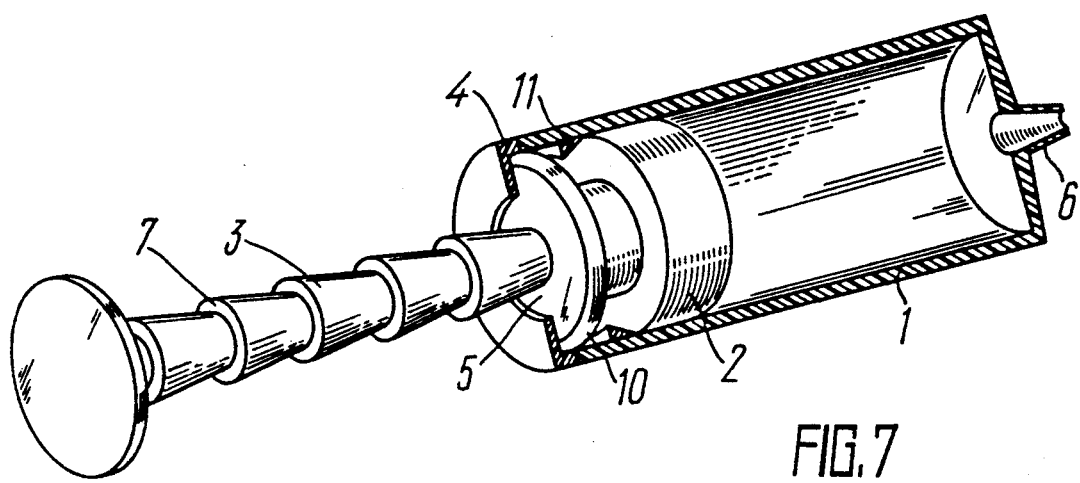
FIG. 7 is an isometric view, partly in longitudinal section, of a disposable injection syringe after drawing an injection substance.

The motion of the piston 2 in the opposite direction is impossible, since the diameter of the greater bases of the cone frustums 9 of the insert 8 exceeds the diameter of the hole 5 in the cover 4 of syringe body 1; besides such a reverse motion is prevented by the profile of the outer surface of the insert 8. Once the injection substance has been drawn, the washer 10 interacts through its outer surface with the bevelled surface 12 of the collar 11 on the inner surface of the syringe body 1, passes beyond the collar 11 and remains in the space between the inner surface of the cover 4 of the syringe body 1 and the surface 13 of the collar 11. Once the washer 10 has passed beyond the collar 11 its return motion becomes impossible, since the diameter of the washer face that faces the collar 11 with the washer 10 in that position, is in excess of the hole restricted by the collar 11. As soon as the washer 10 gets into the space between the cover 4 and the collar 11, the insert 8 happens to be beyond the limits of the body 1 so that the parts 8a, 8b of the insert, while meeting no resistance, are detached from the rod 3 and are free to fall outside (FIG. 7).

Figure 8:
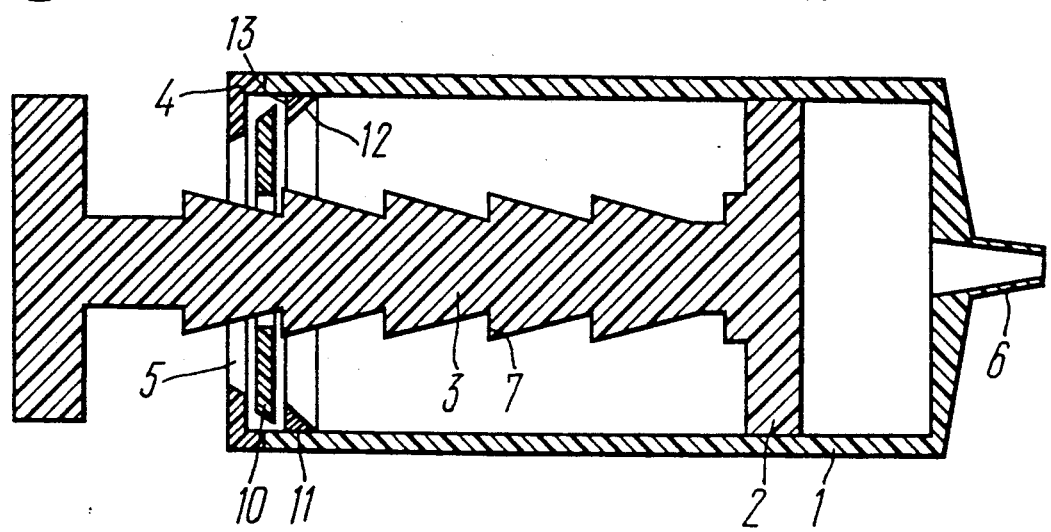
FIG. 8 is a view of FIG. 6 showing a disposable injection syringe at the instant of injection.

When injecting the medicinal substance the rod 3 moves towards the front face 6 of the syringe body 1 (FIG. 8). As a result, the cone frustums 7 of the rod 3 pass, with a small resistance, through the centre hole of the washer 10, whose diameter is approximately equal to a minimum diameter of the rod 3. Return motion of the rod 3 is impossible, since the diameter of the greater bases of the cone frustums 7 of the rod 3 exceeds the diameter of the centre hole of the washer 10.

This makes it impossible to reuse the disposable syringe for repeated injections.

Once the injection has been carried out, the syringe becomes unfit for further use and is subject to reclamation.

Widespread application of the proposed syringe will practically rule out infection of patients with the virus of AIDS, infectious hepatitis, and other diseases transmissible by parenteral administration of medicinal substances.

INDUSTRIAL APPLICABILITY

The disposable injection syringe is applicable at any medical institutions and for individual use.

What is claimed is:

1. A disposable injection, comprising a cylindrical body (1) accommodating a piston (2) with a rod (3), a hole (5) in the rear face of the body (1) for the rod (3) to pass outside, and an injection needle fixing device located in the front face of the body, characterized in that the rod (3) is of a shaped design composed of a plurality of cone frustums (7) arranged consecutively along the rod length and having their greater and lesser bases respectively equal to one another, said cone frustums facing the piston (2) with their lesser bases, a shaped hollow insert (8) is arranged in the body (1) concentrically to the rod (3) so as to encompass the latter, said insert having joints located lengthwise the axis of the rod (3), which insert is composed of at least two parts (8a, 8b), the inner surface of said insert follows the outer surface of the rod (3), while outer surface of said insert is formed by the surfaces of a plurality of cone frustums (9) arranged consecutively along the axis of the rod (3) and coaxially therewith, the greater and lesser bases of said cone frustums being respectively equal to one another, said cone frustums facing the piston (2) with their greater bases, whereas the diameter of the hole (5) in the rear face of the body (1) is selected to be approximately equal to a minimum outside diameter of the insert (8), a washer (10) being interposed between the piston (2) and the insert (8) concentrically to the rod (3), the diameter of a hole in said washer being approximately equal to a minimum diameter of the rod (3), while the side face of said washer is bevelled so that the diameter of face of the washer (10) on the side of the piston (2) exceeds the diameter of the face of the washer (10) on the side of the insert (8), and a collar (11) is provided on the surface of the body (1) nearby the rear face thereof, said collar having its surface (12) bevelled so as to suit the bevelled surface of the washer (10), while a minimum diameter of said collar is approximately equal to a minimum outside diameter of the washer (10).

* * * * *